US008026238B2

(12) United States Patent
Davey et al.

(10) Patent No.: US 8,026,238 B2
(45) Date of Patent: *Sep. 27, 2011

(54) TOPICAL ANTIFUNGAL COMPOSITION

(75) Inventors: Greg Davey, Rowville (AU); Albert Zorko Abram, Rowville (AU)

(73) Assignee: Stiefel Research Australia, Pty Ltd, Rowville, Victoria (AU)

( * ) Notice: Subject to any disclaimer, the term of this patent is extended or adjusted under 35 U.S.C. 154(b) by 233 days.

This patent is subject to a terminal disclaimer.

(21) Appl. No.: 12/293,000

(22) Filed: Dec. 2, 2008

(65) Prior Publication Data

US 2009/0149473 A1 Jun. 11, 2009

Related U.S. Application Data

(63) Continuation of application No. 09/529,033, filed as application No. PCT/AU98/00867 on Oct. 19, 1998, now Pat. No. 7,553,835.

(30) Foreign Application Priority Data

Oct. 17, 1997 (AU) ........................................ PO9838
Jan. 6, 1998 (AU) ........................................ PP1217

(51) Int. Cl.
*A61K 31/497* (2006.01)
*A61K 8/02* (2006.01)
*A01N 65/00* (2009.01)

(52) U.S. Cl. ........ 514/247; 514/863; 514/864; 514/945; 514/947; 424/1.13; 424/404; 424/401

(58) Field of Classification Search .................. 514/247, 514/863, 864, 945, 947; 424/1.13, 404, 401
See application file for complete search history.

(56) References Cited

U.S. PATENT DOCUMENTS

| | | |
|---|---|---|
| 3,131,152 A | 4/1964 | Klausner |
| 3,330,730 A | 7/1967 | Hernandez |
| 3,395,214 A | 7/1968 | Mummert |
| 3,824,303 A | 7/1974 | Lanzet et al. |
| 3,846,480 A | 11/1974 | Inai et al. |
| 3,968,218 A | 7/1976 | Bouillon et al. |
| 4,335,125 A | 6/1982 | Heeres et al. |
| 4,491,588 A | 1/1985 | Rosenburg et al. |
| 4,569,935 A | 2/1986 | Rosenberg et al. |
| 4,746,675 A | 5/1988 | Makino et al. |
| 4,775,678 A | 10/1988 | Su et al. |
| 4,806,262 A | 2/1989 | Snyder |
| 4,882,182 A | 11/1989 | Halls et al. |
| 4,888,354 A | 12/1989 | Chang et al. |
| 4,915,934 A | 4/1990 | Tomlinson |
| 4,942,162 A | 7/1990 | Rosenberg et al. |
| 4,981,678 A | 1/1991 | Tomlinson |
| 5,008,293 A | 4/1991 | Berger |
| 5,156,765 A | 10/1992 | Smrt et al. |
| 5,167,950 A | 12/1992 | Lins |
| 5,219,877 A | 6/1993 | Shah et al. |
| 5,352,437 A | 10/1994 | Nakagawa et al. |
| 5,397,564 A | 3/1995 | Seki et al. |
| 5,456,851 A | 10/1995 | Liu et al. |
| 5,516,504 A | 5/1996 | Tomlinson |
| 5,578,599 A | 11/1996 | Diani et al. |
| 5,776,430 A | 7/1998 | Osborne et al. |
| 5,783,202 A | 7/1998 | Tomlinson et al. |
| 5,788,155 A | 8/1998 | Martin et al. |
| 5,854,246 A | 12/1998 | Francois et al. |
| 5,935,554 A | 8/1999 | Tomlinson |
| 6,211,250 B1 | 4/2001 | Tomlinson et al. |
| 6,231,875 B1 | 5/2001 | Sun et al. |
| 6,255,313 B1 | 7/2001 | Suzuki et al. |
| 6,267,949 B1 | 7/2001 | Halls |
| 6,284,234 B1 | 9/2001 | Niemiec et al. |
| 6,383,471 B1 | 5/2002 | Chen et al. |
| 6,419,913 B1 | 7/2002 | Niemiec et al. |
| 6,469,015 B1 | 10/2002 | Griffiths et al. |
| 6,482,826 B1 * | 11/2002 | Pierard .................... 514/254.07 |

FOREIGN PATENT DOCUMENTS

| | | |
|---|---|---|
| AU | 411 950 A | 11/1967 |
| AU | 80257/87 A | 4/1988 |
| AU | 35717/93 | 10/1993 |
| AU | 709320 B2 | 9/1996 |
| DE | 36 30 065 A1 | 3/1987 |
| EP | 0156508 A1 | 10/1985 |
| EP | 0331489 A2 | 9/1989 |
| EP | 0 382 619 A1 | 8/1990 |
| EP | 0 160051 B1 | 1/1992 |
| EP | 1 070752 A2 | 1/2001 |

(Continued)

OTHER PUBLICATIONS

Sciarra, et al., "Pharmaceutical Aerosols", ch. 20, pp. 589-618, The Theory and Practice of Industrial Pharmacy, 3rd Ed., Lachman, L., et al., Varghese Publishing House, Bombay, India, (1987).

Handbook of Pharmaceutical Excipients. 1994. Alcohol, pp. 7-9. Handbook of Pharmaceutical Excipients, 2nd edition, Wade, et al., 1994, American Pharmaceutical Association, Washington. The Pharmaceutical Press, London.

Handbook of Pharmaceutical Excipients. 1994. Cetyl Alcohol, pp. 99-103. Handbook of Pharmaceutical Excipients, 2nd edition, Wade, et al., 1994, American Pharmaceutical Association, Washington. The Pharmaceutical Press, London.

(Continued)

*Primary Examiner* — Gina C Yu

(74) *Attorney, Agent, or Firm* — The Nath Law Group; Josh B. Goldberg

(57) ABSTRACT

A topical, foamable composition is provided that includes at least one antifungal agent that is able to penetrate the upper layers of skin and is retained in or on an area to be treated for a prolonged period of time, and that has a residual non-volatile component content of less than 25%. In addition, a method of treating fungal diseases including jock itch, tinea, dandruff and sebborheic dermatitis is provided, and includes applying to the affected area of a patient requiring such treatment an antifungal composition.

54 Claims, 4 Drawing Sheets

FOREIGN PATENT DOCUMENTS

| | | |
|---|---|---|
| ES | 2 064 288 A1 | 1/1995 |
| FR | 2 616 065 A1 | 12/1988 |
| FR | 2 740 685 A1 | 5/1997 |
| JP | 48-92282 | 11/1973 |
| JP | 9-98447 C | 5/1980 |
| JP | 9-5045387 B2 | 5/1989 |
| JP | 2-502822 T | 9/1990 |
| JP | 5-306223 A | 11/1993 |
| JP | 08040899 A | 2/1996 |
| JP | 8-291050 A | 11/1996 |
| JP | 9-188629 | 7/1997 |
| JP | 10-121876 A | 5/1998 |
| JP | 10-158782 | 6/1998 |
| JP | 10-265343 | 10/1998 |
| JP | 2810040 B2 | 10/1998 |
| JP | 2810041 B2 | 10/1998 |
| WO | WO 85/01876 | 5/1985 |
| WO | WO 86/00196 | 1/1986 |
| WO | WO 8807362 | 10/1988 |
| WO | 92/00057 A1 | 1/1992 |
| WO | WO 92/04419 | 3/1992 |
| WO | WO 93/17687 | 9/1993 |
| WO | WO 94/16732 | 8/1994 |
| WO | 96/06613 A1 | 3/1996 |
| WO | WO 96/27376 | 9/1996 |
| WO | WO 97/17075 | 5/1997 |
| WO | WO 98/00179 | 1/1998 |
| WO | WO 98/23291 | 6/1998 |
| WO | WO 88/04896 | 7/1998 |
| WO | WO 98/52525 | 11/1998 |
| WO | WO 99/20250 | 4/1999 |
| WO | WO 99/53923 | 10/1999 |
| WO | WO 00/15193 | 3/2000 |
| WO | WO 00/66172 | 11/2000 |
| WO | WO 01/76541 | 10/2001 |
| WO | WO 01-76605 | 10/2001 |

OTHER PUBLICATIONS

Handbook of Pharmaceutical Excipients. 1994. Polyoxyethylene Sorbitan Fatty Acid Esters, pp. 375-378. Handbook of Pharmaceutical Excipients, 2nd edition, Wade, et al., 1994, American Pharmaceutical Association, Washington. The Pharmaceutical Press, London.

Handbook of Pharmaceutical Excipients. 1994. Propylene Glycol, pp. 407-408. Handbook of Pharmaceutical Excipients, 2nd edition, Wade, et al., 1994, American Pharmaceutical Association, Washington. The Pharmaceutical Press, London.

Handbook of Pharmaceutical Excipients. 1994. Stearyl Alcohol. pp. 498-499. Handbook of Pharmaceutical Excipients, 2nd edition, Wade, et al., 1994, American Pharmaceutical Association, Washington. The Pharmaceutical Press, London.

Handbook of Pharmaceutical Excipients. 1994. Water, pp. 546-549. Handbook of Pharmaceutical Excipients, 2nd edition, Wade, et al., 1994, American Pharmaceutical Association, Washington. The Pharmaceutical Press, London.

Zhang, et al., "Separation of Hydrophobic, Positively Chargeable Substances by Capillary Electrophoresis", Anal. Chem., vol. 67, pp. 2070-2077, (1995).

Physicians' Desk Reference. 1996. Nizoral, pp. 1297-1298. Physician's Desk Reference, vol. 50. Medical Economics Co. Inc., Oradell, N.J.

Physicians' Desk Reference. 1991. Lotrimin AF Antifungal, pp. 702-703. Physician's Desk Reference, vol. 12. Medical Economics Co. Inc., Oradell, N.J.

Physicians' Desk Reference. 1991. Micatin, pp. 632-633. Physician's Desk Reference, vol. 12. Medical Economics Co. Inc., Oradell, N.J.

James, et al., "Structural Features of Imidazole Derivatives that Enhance Styrene Oxide Hydrolase Activity in Rat Hepatic Microsomes", J. Med. Chem., vol. 28, pp. 1120-1124, (1985).

Shuster, "The Aetiology of Dandruff and the Mode of Action of Therapeutic Agents", British Journal of Dermatology, vol. 3, pp. 235-242, (1984).

Ortonne, et al., "Comparative Study of Ketoconazole 2% Foaming Gel and Betamethasone Dipropionate 0.05% Lotion in the Treatment of Seborrhoeic Dermatitis in Adults", Dermatology, vol. 184, pp. 275-280, (1992).

McGrath, et al., "The Control of Seborrhoeic Dermatitis and Dandruff by Antipityrosporal Drugs", Drugs, vol. 41, issue 2, pp. 178-184, (1991).

Ansel, et al., "Aerosols, Inhalations, and Sprays", Pharmaceutical Dosage Forms, ch. 13, pp. 443-459, (1995).

Falbe J; Regitz M: "Rö mpp Chemie Lexikon" 1995, Georg Thieme, Stuttgart (Germany) p. 1337-p. 1338.

Ansil et al. "Pharmaceutical Dosage Forms and Drug Delivery Systems" (1990), 5$^{th}$ ed. p. 244, Lea & Febiger, Malvern, PA.

Electronic Orange Book, Search results from "Rx" table for query on ketoconazole (1 pg.), Oct. 2004.

Electronic Orange Book, Search results from the "Rx" table for query on App. No. 019084 (1pgs.), Oct. 2004.

Woodford R., et al. "Bioavailability and Activity of Topical Corticosteroids from a Novel Drug Delivery System, the Aerosol Quick-Break Foam", Received from School of Pharmacy and Pharmacal Sciences, vol. 66, No. 1, Jan. 1977, Purdue University.

Abram, A.Z., et al. "Mousses", Jun. 2001, Chapter 19, pp. 221-232, Soltec Research Pty Ltd., Rowville, Victoria Australia.

* cited by examiner

FIG. 1 KETOCONAZOLE RETAINED IN SKIN VERSUS
TIME AFTER APPLICATION OF FORMULATION.
DATA ARE THE MEAN ± (n=30) FROM TABLE 1

$y = 7579.3x + 90.4 \quad r^2 = 1.0$

TOPICAL ANTIFUNGAL COMPOSITION

BACKGROUND OF THE INVENTION

The present invention relates to a foamable antifungal composition for the treatment of various skin conditions.

Antifungal agents are well known, and include macrolide antibiotics such as griseofulvin, and imidazoles such as clotrimazole and ketoconazole.

Ketoconazole was originally described by Heeres et al in U.S. Pat. No. 4,335,125, in which its principal utility was an antifungal compound useful in the treatment of a variety of conditions including sebborheic dermatitis, dandruff, "jock itch" and tinea.

Antifungal compositions are traditionally applied as lotions or creams. There are however disadvantages to these forms. In particular, the formulations are frequently very viscous requiring substantial rubbing to achieve penetration into the effected area, an act in itself which causes discomfort and sometimes irritation. If the viscous formulations are not vigorously applied, the active antifungal agent does not necessarily reach the site requiring treatment being the epidermis of the skin. Non-viscous creams and lotions are wont to flow off the effected site before penetration is achieved. One final disadvantage is that cream and lotion bases in themselves can add to site irritation depending on their content.

Ketoconazole was disclosed in U.S. Pat. No. 4,569,935 to be useful in the topical treatment of psoriasis and seborrheic dermatitis. Pursuant to this utility, ketoconazole has been marketed in a 2% shampoo formulation for the treatment of scaling due to dandruff, sold under the brand name "Nizoral®". This shampoo is applied by the user and then removed shortly, for example 3-5 minutes, after its application by rinsing with water. The active agent is thus only in contact with the area to be treated for a very limited time.

Another patent describing ketoconazole based shampoos is U.S. Pat. No. 5,456,851 in the name of JOHNSON & JOHNSON CONSUMER PRODUCTS, INC which aims to provide good cosmetic properties to the shampoo including lather, and to retard degradation of the ketoconazole. This composition is a foaming formulation.

The disadvantage of such shampoo formulations is that during normal usage, the formulation does not remain on the scalp for a period of time sufficient to allow the antifungal agent to achieve its maximal therapeutic effect since they are designed to be applied, for example in the shower or bath, and shortly after rinsed off with water. Typically, the application instructions for such shampoos suggest that the formulation be removed after 3-5 minutes.

In order to achieve maximal therapeutic effect, one alternative such as is described in AU 80257/87, is to provide a high quantity of residual solids which remain after application to treat the offending skin condition. There is disclosed in AU 80257/87 a foam composition for the delivery of minoxidil. The formulations disclosed in this document all contain a high percentage of non-volatile residues, including propylene glycol. While it is not disclosed why these formulations contain such a large amount of propylene glycol, it is postulated that the propylene glycol is probably required either to enhance the penetration and/or to improve the solubility of the minoxidil. The disadvantage of a composition with a high residual content is that the non-volatile residues are retained at the site of application and therefore feel unpleasant and unattractive to the user.

Alternatives to ketoconazole and minoxidil are described in AU-A-35717/93 in the name of SMITH KLINE BEECHAM PLC which discloses compositions including a novel androstene steroid for use in the treatment of acne and sebborrhea, and AU-A-48851/96 in the name of MEDEVA PLC which describes the use of betamethasone in a quick breaking foam including a buffering agent for use in the treatment of skin diseases and particularly scalp psoriasis.

It is an aim of this invention to provide an antifungal composition which is effective in its treatment of fungal skin conditions but which is also pleasant to use.

SUMMARY OF THE INVENTION

To this end, in a first aspect of the invention, there is provided a topical, foamable composition including at least one antifungal agent, said composition characterised in that said at least one antifungal agent is able to penetrate the upper layers of the skin and is retained in or on an area to be treated for a prolonged period of time, and in that it has a residual non-volatile component content of less that 25%.

It has been surprisingly found that the antifungal composition of the present invention has a commercially acceptable cosmetic appeal and during normal usage allows greater penetration and retention of the antifungal agent in the upper layers of the skin, particularly in the epidermis, thus providing a reservoir of active agent available to achieve a sustained antifungal effect when compared against known formulations. This latter feature leads to enhanced pharmaceutical appeal as well as cosmetic appeal. Moreover, the residual solids content of the formulation is so low as to not provide discomfort and irritation to the user The term "prolonged period of time" is meant to encompass periods of time sufficiently long so as to enable the active agent present to be substantially fully absorbed by the organism being treated, or substantially fully metabolised by the patient being treated.

In a preferred embodiment, the one or more antifungal agents is selected from the group consisting of diols, allylamines (including naftifine and terbinafine), polyene macrolide antibiotics (including amphotericin and nystatin), triazole derivatives (such as fluconazole), fatty acids (such as caprylic and propionic acid), amorolfine, ciclopirox, olamine, benzoic acid, flucytosine, haloprogin, tolnaftate, undecenoic acid and its salts, griseofulvin and imidazole compounds. More preferably, the antifungal is an imidazole compound. Most preferably, the antifungal agent is ketoconazole or chlorphenesin (3-(4-Chlorphenoxy)propane-1,2-diol).

Preferably the compositions according to the invention have a residual non-volatile component content of less that 10%, and more preferably of less than 6%.

In a preferred embodiment the topical, foamable composition is provided as a mousse.

In a further preferred embodiment the mousse is a temperature sensitive mousse, which breaks down rapidly when exposed to the skin temperature.

In a still further embodiment, the composition is an ethanolic mousse including a lower alcohol content of greater than 10%, more preferably greater than 50% and a hydrocarbon gas content propellent of less than 60%, more preferably less than 10%.

In an alternative embodiment the composition is an aqueous mousse including no lower alcohol content and a hydrocarbon gas content propellent of less than 60%, more preferably less than 10%.

(Unless specified otherwise in the specification, all % are based on the total weight of the composition.)

In the temperature sensitive mousse, the long chain alcohol may be chosen from, for example, cetyl, stearyl, lauryl, myristyl and palmityl alcohols and mixtures of two or more thereof.

The lower alcohol may preferably be chosen from methyl, ethyl, isopropyl and butyl alcohols, and mixtures of two or more thereof. Ethanol has been found to be particularly preferred.

Surfactants utilised in the temperature sensitive mousse may preferably be chosen from ethoxylated sorbitan stearate, palmitate, oleate, nonyl phenol ethoxylates and fatty alcohol ethoxylates, and mixtures of two or more thereof. Thus, for example, Polysorbate 60 (a mixture of partial stearic esters of sorbitol and its anhydrides copolymerised with approximately 20 moles of ethylene oxide for each mole of sorbitol and its anhydrides) has been found to be particularly preferred. The surfactant enhances the long chain alcohol solubility in the system and enhances mousse formation.

In a further aspect of the invention, there is provided a foamable composition including
up to 5% of long chain alcohols
up to 5% of quaternary compound
up to 10% of propylene glycol
up to 5% of antifungal agent
up to 90% of lower alcohol solvent
up to 5% of surfactant
5-95% of water, and
up to 20% of a hydrocarbon gas propellant Preferably, the long chain alcohol is cetyl or stearyl alcohol or mixtures thereof.

Preferably, the quaternary compound is quaternium oxy ethyl alkyl ammonium phosphate commercially available under the trade name, Dehyquart SP.

Preferably, the lower alcohol solvent is ethanol or propanol or mixtures thereof.

Suitable gas propellants include non-toxic gas propellants suited to foamable cosmetic and pharmaceutical compositions and known to those skilled in the art.

Thus, one may select the propellant from propane, butane, dichloro difluoro methane, dichloro tetrafluoro ethane, octafluoro cyclobutane, and mixtures of two or more thereof. It is necessary to select a propellant most compatible with the entire system. The maximum level of propellant will be determined as the amount miscible with the utilized water/lower alcohol ratio. In addition to acting as a propellant, the propellant will also act as a solvent for the long chain alcohol and active substances in the aqueous/alcoholic system.

In a second aspect of the invention there is provided a composition for the treatment of fungal skin conditions including dandruff, seborrheic dermatitis, tinea, jock itch and the like, said composition characterised in that it is a foamable mousse applicable to the skin of the user in the substantial absence of water and without substantially immediate removal by washing.

In a preferred embodiment of this aspect of the invention, said composition has a non-volatile component content of less than 25%, preferably less than 10% and more preferably less than 6%.

In a more preferred embodiment of this aspect of the invention, the mousse is a temperature sensitive mousse, which breaks down rapidly when exposed to the skin temperature.

In a still further preferred embodiment, the composition is a mousse including a lower alcohol content of greater than 10%, more preferably greater than 50% and a hydrocarbon gas content propellent of less than 60%, more preferably less than 10%.

In a further aspect of the invention there is provided a topical, foamable composition including an antifungal agent characterised in that upon application to the skin of a user a penetration of at least 10 µg/cm$^2$ is achieved in the epidermis within one hour of application and sustained over a period of at least 23 hours.

When the preferred active agent is ketoconazole, the invention provides a topical, foamable composition characterised in that upon application to the skin of a user a penetration of at least 30 µg/cm$^2$ is achieved in the epidermis within one hour of application and sustained over a period of at least 23 hours.

When the preferred active agent is chlorphenesin, the invention provides a topical, foamable composition characterised in that upon application to the skin of a user a penetration of at least 10 µg/cm$^2$ is achieved in the epidermis within one hour of application and sustained over a period of at least 23 hours.

In a still further aspect of the invention, there is provided a method of treating fungal infections, particularly tinea, jock itch, dandruff and sebborheic dermatitis by applying to the affected area of a patient requiring such treatment the antifungal composition of the present invention.

In a preferred embodiment of this aspect of the invention, the composition is allowed to remain on the affected area for an extended period of time.

In this context "extended period of time" means a length of time greater than the length of time that prior art topical compositions such as shampoos are prescribed to remain in contact with the affected area. Usually, shampoos are designed to be washed off within 5 minutes.

More preferably, when the composition is used to treat dandruff or sebborheic dermatitis, it is applied at one wash or between washes and is allowed to remain on the site of application such as the scalp or hair until the site of application is subsequently washed again.

The invention also encompasses the use of an antifungal agent in the preparation of a topical foamable composition for the treatment of fungal diseases including dandruff, tinea, jock itch and sebborheic dermatitis, the topical foamable composition being characterised in that it is able to penetrate the epidermis of the skin and is retained in or on an area to be treated for a prolonged period of time, and in that it has a non-volatile component content of less that 25%.

BRIEF DESCRIPTION OF THE DRAWINGS

The present subject matter can be understood with reference to the following drawings.

DETAILED DESCRIPTION OF THE INVENTION

Figure 1:
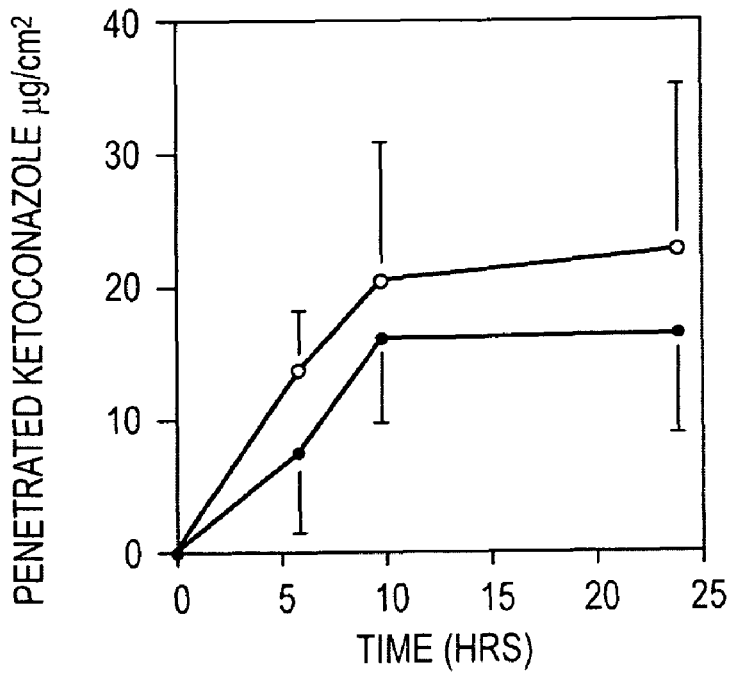
FIG. 1 is a graphical representation of the time course of the ketoconazole penetrating across human epidermis to receptor fluid.

Two formulations of the present invention were prepared.

| 1) 0.5% ketoconazole mousse composition | |
|---|---|
| Cetyl alcohol | 1.10 |
| Stearyl alcohol | 0.50 |
| Quaternium 52 (50%) | 1.00 |
| Propylene Glycol | 2.00 |
| Ketoconazole USP | 0.50 |
| Ethanol 95PGF3 | 60.55 |
| Deionised Water | 30.05 |
| P75 Hydrocarbon Propellant | 4.30 |
| 2) 1% ketoconazole mousse composition | |
| Cetyl alcohol | 1.10 |
| Stearyl alcohol | 0.50 |
| Quaternium 52 (50%) | 1.00 |
| Propylene Glycol | 2.00 |
| Ketoconazole USP | 1.00 |
| Ethanol 95PGF3 | 60.20 |
| Deionised Water | 29.90 |
| P75 Hydrocarbon Propellant | 4.30 |

The compositions were prepared by dissolving the active in the ethanol. the cetyl and stearyl alcohol are then added to the heated solution and mixed until dissolved. The quaternium 52, propylene glycol and water are then added and stirred until homogenous, while maintaining the elevated temperature. The solution is then dispensed into aerosol cans where the aerosol valve is then fitted and the can charged with propellant.

EXAMPLE 1

A study was undertaken to compare the epidermal penetration of the two mousse compositions above, against the commercially available Nizoral® shampoo containing 2% ketoconazole. In particular the respective formulations were applied and removed as for a conventional shampoo so as to compare the penetration of the respective formulations into the epidermis.

Equipment and Materials
  in vitro Franz diffusion cells (surface area 1.33 cm$^2$, receptor volume 3.5 ml) incorporating human epidermis
  HPLC equipment: Shimadzu automated HPLC system with uv detector, bovine serum albumin dissolved in phosphate buffered saline (pH 7.4) as receptor phase to mimic physiological conditions.
Experimental Protocol
  finite dosing (50 mg for shampoo and 100 mg for mousses)
  receptor phase: 4% BSA in phosphate buffered saline at pH 7.4 sampling time: 6, 10, 24 hours (amount in receptor phase (µg/cell) and epidermis (µg/cell)) non-occlusion study
  each time period and formulation conducted in triplicate.
Application Procedure
Shampoo: 50 mg shampoo (equivalent to 1 mg ketoconazole) dose applied to pre-wetted skin with stirring and rinsed off with deionised water after 4 minutes.
Mousse: 100 mg mousse (equivalent to 1 mg ketoconazole for 1% mousse and 500 µg ketoconazole for 0.5% mousse dose applied (not rinsed off).
Epidermal Retention Protocol
  Epidermis removed from cell following time interval, rinsed with distilled water and dried to remove ketoconazole remaining on surface. Ketoconazole extracted from epidermal sample by soaking in methanol for 1 hour. This procedure is repeated with a second volume of methanol for 30 mins. The methanol samples are combined for HPLC analysis (this procedure has been validated with a 99% recovery rate).
HPLC Assay

| | |
|---|---|
| Column: | Nova Pak C$_{18}$ steel column, 3.9 × 150 mm |
| Mobile phase: | 70% MeOH in 0.02 M phosphate buffer, pH 6.8 |
| Wavelength: | 254 nm |
| Flow rate: | 1.3 ml/min |
| Injection volume: | 10 µl |
| Retention time: | about 7 min |

Results
  Table 1 shows the cumulated ketoconazole in both the receptor phase and the epidermis at defined time points following application of the mousse according to the invention and the shampoo of the prior art.

TABLE 1

| | Ketoconazole µg/cell | | | | | |
|---|---|---|---|---|---|---|
| | 6 hours | | 10 hours | | 24 hours | |
| Sample | receptor | epidermis | receptor | epidermis | receptor | epidermis |
| 0.5% mousse | 4.96 | 33.15 | 9.04 | 69.46 | 14.69 | 42.10 |
| 0.5% mousse | 2.83 | 35.71 | 18.06 | 48.04 | 24.77 | 39.19 |
| 0.5% mousse | 14.37 | 34.3 | 21.3 | 55.29 | 9.82 | 48.27 |
| Mean ± SD | 7.4 ± 6.1 | 34.4 ± 1.3 | 16.1 ± 6.4 | 57.6 ± 10.9 | 16.4 ± 7.6 | 43.2 ± 4.6 |
| 1% mousse | 12.86 | 46.4 | 31.50 | 67.51 | 21.90 | 51.43 |
| 1% mousse | 10.03 | 61.8 | 11.05 | 55.65 | 35.85 | 46.64 |
| 1% mousse | 18.61 | 38.6 | 19.38 | 56.83 | 10.72 | 43.28 |
| Mean ± SD | 13.8 ± 4.4 | 48.9 ± 11.8 | 20.6 ± 10.3 | 60 ± 6.5 | 22.8 ± 12.6 | 47.1 ± 4.1 |
| 2% shampoo | N | N | N | 0.89 | N | N |
| 2% shampoo | N | N | N | 0.28 | N | 0.38 |
| 2% shampoo | N | N | N | N | N | 0.34 |
| Mean ± SD | — | — | — | 0.39 ± 0.46 | — | 0.24 ± 0.21 |

N: not detectable (assuming to be zero for calculating mean and SD)
—: not available Table 2 shows the cumulated ketoconazole in both receptor (expressed as μg/ml receptor fluid) and epidermis (expressed as μg/cm² surface area) at defined time points following application of the mousse according to the present invention and the shampoo of the prior art.

TABLE 2

| | Ketoconazole μg | | | | | |
|---|---|---|---|---|---|---|
| | 6 hours | | 10 hours | | 24 hours | |
| Sample | receptor | epidermis | receptor | epidermis | receptor | epidermis |
| 0.5% mousse | 1.42 | 26.95 | 2.58 | 56.47 | 4.20 | 34.23 |
| 0.5% mousse | 0.81 | 29.03 | 5.46 | 39.06 | 7.08 | 31.86 |
| 0.5% mousse | 4.11 | 27.89 | 6.09 | 44.95 | 2.81 | 39.24 |
| Mean ± SD | 2.11 ± 1.76 | 27.96 ± 1.04 | 4.61 ± 1.82 | 46.83 ± 8.86 | 4.70 ± 2.18 | 35.11 ± 3.77 |
| 1% mousse | 3.67 | 37.72 | 9.00 | 54.89 | 6.26 | 41.81 |
| 1% mousse | 2.87 | 50.24 | 3.16 | 45.24 | 10.24 | 37.92 |
| 1% mousse | 5.32 | 31.38 | 5.54 | 46.20 | 3.06 | 35.19 |
| Mean ± SD | 3.95 ± 1.25 | 39.78 ± 9.60 | 5.90 ± 2.94 | 48.78 ± 5.31 | 8.52 ± 3.80 | 38.31 ± 3.33 |
| 2% shampoo | N | N | N | 0.72 | N | N |
| 2% shampoo | N | N | N | 0.23 | N | 0.31 |
| 2% shampoo | N | N | N | N | N | 0.28 |
| Mean ± SD | — | — | — | 0.32 ± 0.37 | — | 0.20 ± 0.17 |

N: not detectable (assuming to be zero for calculating mean and SD)
—: not available FIG. 1 shows the time course of the ketoconazole penetrating across human epidermis to receptor fluid. The closed points of the graph represent 0.5% mousse, the open points represent 1.0% mousse. Data are the mean±SD of triplicate (from Table 2).

Figure 2:
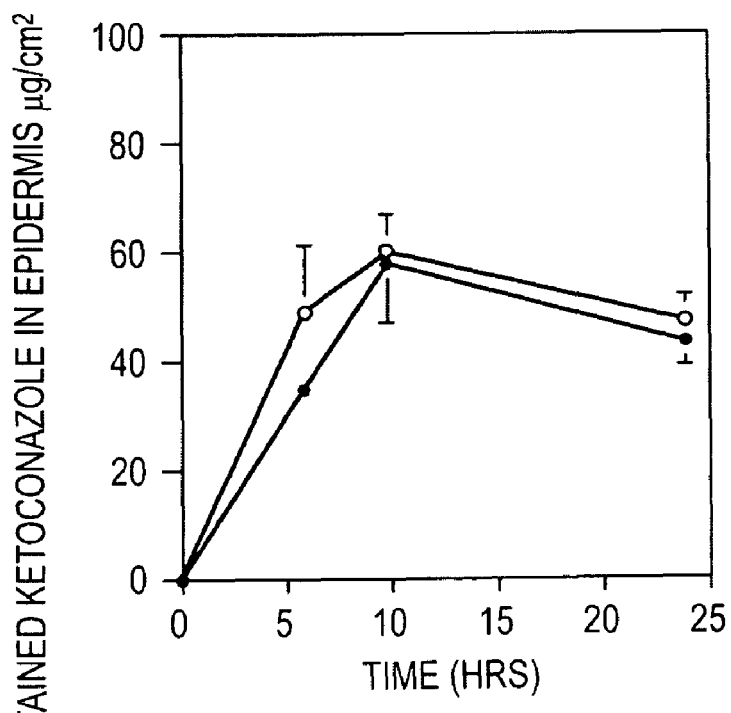
FIG. 2 is a graphical representation of the time course of ketoconazole retained in the epidermis.

FIG. 2 represents the time course of ketoconazole retained in the epidermis. The closed points of the graph represent 0.5% mousse, the open points represent 1.0% mousse. Data are the mean±SD of triplicate (from Table 2).

Figure 3:
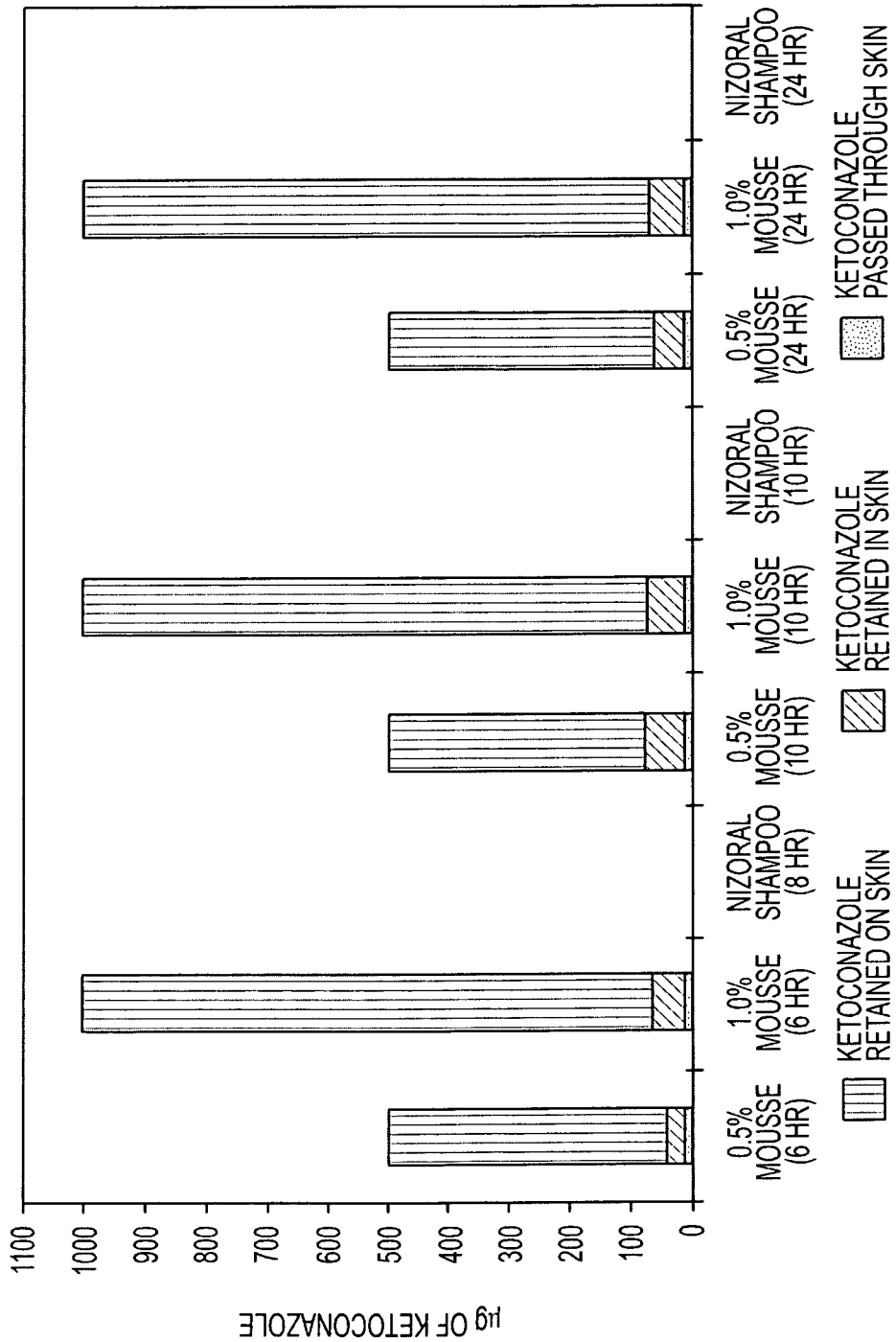
FIG. 3 is a graphical representation of the levels of retention of ketoconazole on the skin, the levels of retention of the ketoconazole in the skin and the amount of ketoconazole passed through the skin in the tests using a mousse according to one embodiment of the present subject matter with the same measures using Nizoral®.

FIG. 3 compares the levels of retention of ketoconazole on the skin, the levels of retention of the ketoconazole in the skin and the amount of ketoconazole passed through the skin in the tests using a mousse according to the invention with the same measures using Nizoral®. Note that ketoconazole levels found after application of the Nizoral® shampoo were low and thus are not visible in this figure It can readily be observed from the results of example 1 that:
1. the ketoconazole in the mousse compositions of the present invention penetrated the skin in appreciable quantity;
2. the ketoconazole in the mousse composition of the present invention was preferentially retained in the epidermis compared to penetration into the receptor solution;
3. application of the prior art shampoo, Nizoral®, resulted in insignificant amounts of ketoconazole in the epidermis and penetrating to the receptor phase at any of the time points following application using a standardised shampooing procedure;
4. comparison of the 1% and 0.5% mousse formulations of the present invention shows that there is little difference in epidermal and receptor phase concentrations.

EXAMPLE 2

A second study was undertaken to compare the skin penetration and retention of ketoconazole from the 1% ketoconazole mousse composition of the current invention with Nizoral® Shampoo (1% w/w). The 1% mousse composition had a total residue content of 5.1% solids including active.

Equipment and Materials

In vitro Franz diffusion cells (surface area 1.33 cm², receptor volume 3.5 mL) incorporating full thickness human skin, HPLC equipment: Shimadzu automated HPLC system with uv detector.

Experimental Protocol

Finite dosing (50 mg of each formulation placed onto skin surface),

Receptor phase: 4% bovine serum albumin (BSA) in phosphate buffered saline (PBS) pH 7.4, Sampling times for skin retention: 15 minutes, 1, 12, 24 hours, Sampling times for skin penetration to receptor phase: 12, 24 hours, Amount of ketoconazole in full thickness skin and receptor phase measured by HPLC assay following suitable extraction procedure, Non-occlusion study, Triplicate measurements.

Application Procedure

Both mousse and shampoo were applied and left in contact with the skin for the duration of the penetration study. Following this the formulation was washed off the skin with distilled water prior to sample extraction procedure and HPLC assay for ketoconazole content.

HPLC Assay

| | |
|---|---|
| Column: | Nova Pac $C_{18}$ steel column, 3.9 × 150 mm (Waters) |
| Mobile phase: | 70% MeOH in 0.02M PBS, pH 6.8 |
| Wavelength: | 254 nm |
| Flow rate: | 1.0 mL/min |
| Injection volume: | 10 μL |
| Retention time: | approximately 8 mins |

Full Thickness Skin Retention Protocol

Full thickness skin was removed from cell following time interval, rinsed with distilled water and dried to remove ketoconazole remaining on surface. Ketoconazole was extracted from full thickness skin sample by soaking in methanol for 1 hour. This procedure was repeated with a second volume of methanol for 30 mins. The methanol samples were combined from HPLC analysis. [This procedure has been validated with a 99% recovery rate].

Results

Figure 4:
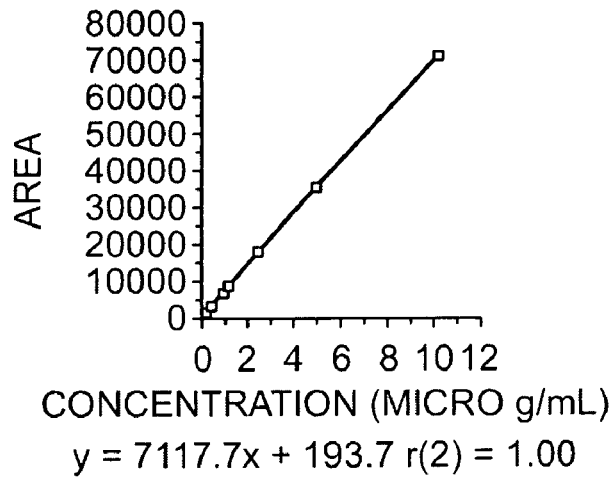
FIG. 4 is a graphical representation of the HPLC standard curve for ketoconazole.

FIG. 4 shows the HPLC standard curve for ketoconazole.

Table 3 shows the amount of ketoconazole retained in the skin ($\mu g/cm^2$) at 15, 60 minutes, 12 and 24 hours following application of the mousse according to the invention, or the shampoo of the prior art.

TABLE 3

Ketoconazole retained in skin ($\mu g/cm^2$) at 15, 60 mins, 12, 24 hours following application of mousse or shampoo.

| | Ketoconazole in skin ($\mu g/cm^2$) mean ± SEM | | | |
|---|---|---|---|---|
| Sample | 15 mins | 60 mins | 12 hrs | 24 hrs |
| Shampoo | 11.2 ± 0.91 | 24.2 ± 1.58 | 39.7 ± 12.3 | 70.1 ± 18.8 |
| Mousse | 19.6 ± 2.5 | 44.1 ± 8.27 | 128.37 ± 19.1 | 228.57 ± 14.8 |

Table 4 shows the amount of ketoconazole penetrated to the receptor phase ($\mu g/mL$) at 12, 24 hours following application of the mousse according to the invention, or the shampoo of the prior art.

TABLE 4

Ketoconazole penetrated to receptor phase ($\mu g/mL$) at 12, 24 hours following application of mousse or shampoo.

| | Ketoconazole in receptor ($\mu g/mL$) mean ± SEM | | | |
|---|---|---|---|---|
| Sample | 15 mins | 60 mins | 12 hrs | 24 hrs |
| Shampoo | — | — | n | 0.04 ± 0.04 |
| Mousse | — | — | 0.07 ± 0.05 | 0.30 ± 0.04 | n: not detectable
—: not assayed

Figure 5:
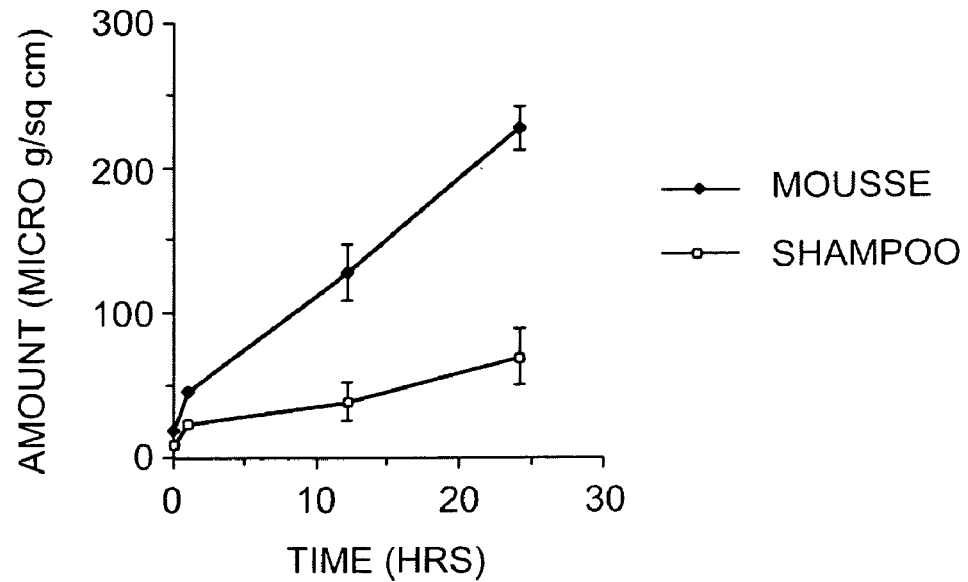
FIG. 5 is a graphical representation of the amount of ketoconazole retained in the skin versus the time after application of the formulation according to one embodiment of the present subject matter.

FIG. 5 shows the amount of ketoconazole retained in the skin versus the time after application of the formulation according to the invention. Data are the mean±SEM (n=3) from Table 4.

The mousse formulation according to the invention demonstrated significantly greater skin retention of ketoconazole than the shampoo formulation of the prior art over the 24 hour period.

It can readily be observed from the results of example 2 that:
1. penetration of ketoconazole to the receptor phase over the 24 hours following application was minimal for both shampoo and mousse.
2. skin retention of ketoconazole was significantly greater following application of the mousse formulation compared to the shampoo (p<0.05).

EXAMPLE 3

A third study was undertaken to compare the skin penetration and retention of two formulations according to the invention in which the active anti fungal agent was chlorphenesin (0.5% w/w). One formulation was ethanolic and had a total residue content of 2.5% solids including active, the other formulation was aqueous and had a total residue content of 4.6% solids including active.

Aqueous Formulation

| | % w/w |
|---|---|
| Chlorphenesin | 0.50 |
| Cetyl alcohol | 0.70 |
| Stearyl alcohol | 0.30 |
| Icocetyl alcohol | 2.50 |
| Ceteth 20 | 0.50 |

-continued

| | % w/w |
|---|---|
| Preservative | 0.10 |
| Purified Water | 90.40 |
| P75 Hydrocarbon Propellant | 5.00 |

Ethanolic Formulation

| | % w/w |
|---|---|
| Chlorphenesin | 0.50 |
| Cetyl alcohol | 1.10 |
| Stearyl alcohol | 0.50 |
| Polysorbate | 0.40 |
| Ethanol 95% | 60.79 |
| Purified Water | 32.41 |
| P75 Hydrocarbon Propellant | 4.30 |

Equipment and Materials

In vitro Franz diffusion cells (surface area 1.33 $cm^2$, receptor volume 3.5 mL) incorporating full thickness human skin,
HPLC equipment: Shimadzu automated HPLC system with uv detector.

Experimental Protocol

Finite dosing (50 mg of each formulation placed onto skin surface),
Receptor phase: 4% bovine serum albumin (BSA) in phosphate buffered saline (PBS) pH 7.4,
Sampling times for skin retention: 15 minutes, 1, 12, 24 hours,
Sampling times for skin penetration to receptor phase: 12, 24 hours,
Amount of chlorphenesin in full thickness skin and receptor phase measured by HPLC assay following extraction into acetonitrile (ACN) and methanol (MeOH) (9:1),
Non-occlusion study,
Triplicate measurements.

Application

Mousses according to the invention were applied and left in contact with the skin for the duration of the penetration study.

Following this the formulation was washed off with distilled water prior to the extraction and HPLC for chlorphenesin content.

HPLC Assay

| | |
|---|---|
| Column: | Nova Pac $C_{18}$ steel column, 3.9 × 150 mm (Waters) |
| Mobile phase: | 30% ACN |
| Wavelength: | 280 nm |
| Flow rate: | 1.0 mL/min |
| Injection volume: | 20 µL |
| Retention time: | approximately 3.6 mins |

Skin Retention Protocol

Skin was removed form the cell following time interval and rinsed with distilled water to remove chlorphenesin on the surface. Chlorphenesin was extracted from homogenised skin by soaking in 1 mL ACN-MeOH mix for 1 hour. This procedure was repeated for a further four 30 minute periods. The five samples were combined for HPLC analysis. [The procedure was validated with a 99% recovery rate].

Results

Figure 6:
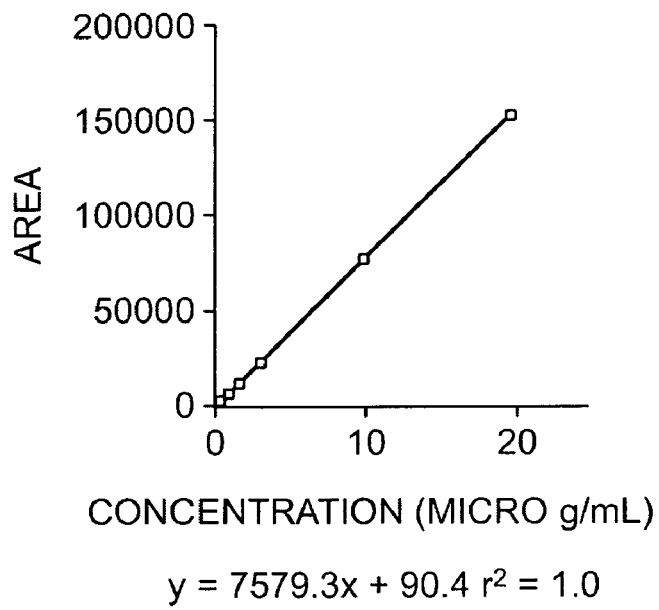
FIG. 6 is a graphical representation of the HPLC standard curve for chlorphenesin.

FIG. 6 shows the HPLC standard curve for chlorphenesin. Data are the mean±standard deviation (n=3).

Table 5 shows the amount of chlorphenesin retained in the skin (µg/cm$^2$) at 15, 60 minutes, 12 and 24 hours following application of the mousse according to the invention.

TABLE 5

| | Chlorphenesin in skin (µg/cm$^2$) mean ± SD | | | |
|---|---|---|---|---|
| Sample | 15 mins | 60 mins | 12 hrs | 24 hrs |
| aqueous | 12.8 ± 4.8 | 13.2 ± 1.1 | 47.6 ± 13.2 | 35.8 ± 2.2 |
| non-aqueous | 16.7 ± 5.5 | 22 ± 9.7 | 93.8 ± 17.3 | 57.4 ± 20.4 |

Table 6 shows the amount of chlorphenesin penetrated to the receptor phase (µg/mL) at 12, 24 hours following application of the mousse according to the invention.

TABLE 6

| | Chlorphenesin in receptor (µg/mL) mean ± SD | | | |
|---|---|---|---|---|
| Sample | 15 mins | 60 mins | 12 hrs | 24 hrs |
| aqueous | — | — | 2.9 ± 0.4 | 5.6 ± 1.1 |
| non-aqueous | — | — | 5 ± 0.7 | 5.1 ± 1.5 |

:— not assayed

Figure 7:
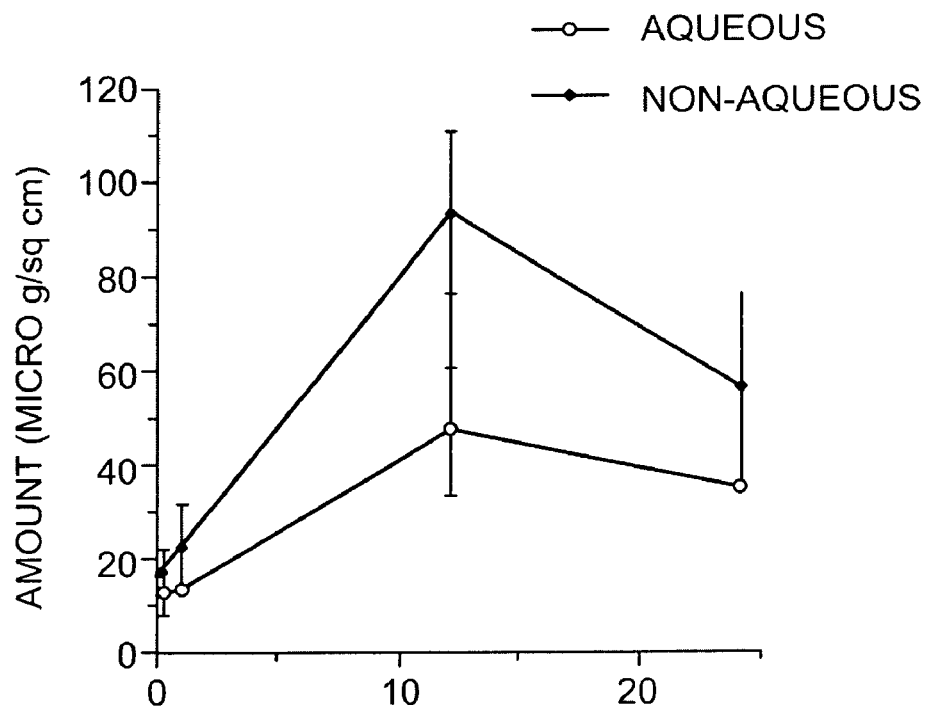
FIG. 7 is a graphical representation of the amount of chlorphenesin retained in the skin versus the time after application of the formulation according to one embodiment of the present subject matter.

FIG. 7 shows the amount of chlorphenesin retained in the skin versus the time after application of the formulation according to the invention. Data are the mean±standard deviation (n=3) from Table 5. The open points are the aqueous formulation. The closed points represent the ethanolic formulation.

It is readily observed from the results of example 3 that active agents other than ketoconazole formulated as both ethanolic and aqueous compositions achieve the desired penetration and retention levels for effective treatment of fungal skin conditions.

It will be appreciated that the scope of this invention goes beyond the specific formulations exemplified to encompass topical foamable antifungal compositions having like components to those specifically mentioned but having characteristic penetration and retention levels in the skin of the user, and low levels of residual solid content as defined.

The claims defining the invention are as follows:

1. A method for treating fungal diseases, comprising:
   (a) providing a topical, foamable composition which in use produces a temperature sensitive, quick-breaking foam or mousse, the composition consisting essentially of:
      one or more antifungal agents selected from the group consisting of an imidazole compound and a triazole compound, wherein the antifungal agent is capable of penetrating the upper layers of skin of a user,
      at least one surfactant,
      water, a lower alcohol, a long chain alcohol, a residual non-volatile component content of less than 25% by weight, and a hydrocarbon gas propellant content of less than 60% by weight; wherein the one or more antifungal agents is dissolved in the lower alcohol; and
   (b) applying the topical, foamable composition to user's skin, whereupon the antifungal agent is retained in or on skin for a period of time sufficient to achieve skin penetration.

2. The method of claim 1, wherein the lower alcohol is ethanol with a content of greater than 50% by weight.

3. The method of claim 1, wherein the content of the residual non-volatile component is less than 10% by weight.

4. The method of claim 1, wherein the provided topical foamable composition consists essentially of:
   up to 5% by weight of long chain alcohol;
   up to 10% by weight of propylene glycol;
   up to 5% by weight of the antifungal agent;
   up to 90% by weight of lower alcohol;
   up to 5% by weight of surfactant;
   5-95% by weight of water; and
   up to 20% by weight of the hydrocarbon gas propellant.

5. The method of claim 1, wherein the antifungal agent is ketoconazole.

6. The method of claim 1, wherein the surfactant is selected from the group consisting of a quaternary compound, ethoxylated sorbitan esters, ethoxylated sorbitan palmitate, ethoxylated sorbitan oleate, a nonyl phenol ethoxylated and a fatty alcohol ethoxylate, and mixtures thereof.

7. A topical, foamable composition, consisting essentially of:
   (a) one or more antifungal agents selected from the group consisting of an imidazole compound and a triazole compound;
   (b) at least one surfactant;
   (c) a lower alcohol content of greater than 50% by weight;
   (d) water;
   (e) a long chain alcohol;
   (f) a residual non-volatile component content of less than 25% by weight; and
   (g) a propellant;
   wherein the one or more antifungal agents is dissolved in the ethanol; and
   wherein the composition produces a temperature-sensitive, quick-breaking foam or mousse when used.

8. The composition of claim 7, wherein the content of the residual non-volatile component is less than 10% by weight.

9. The composition of claim 7, wherein the composition is a mousse.

10. The composition of claim 9, wherein the propellant is a hydrocarbon gas propellant in an amount of less than 60% by weight.

11. The composition of claim 7, wherein the lower alcohol is ethanol.

12. The composition of claim 7, consisting essentially of:
   up to 5% by weight of long chain alcohol;
   up to 10% by weight of propylene glycol;
   up to 5% by weight of the antifungal agent;
   up to 90% by weight of lower alcohol;
   up to 5% by weight of surfactant;
   5-95% by weight of water; and
   up to 20% by weight of hydrocarbon gas propellant.

13. The composition of claim 7, wherein the antifungal agent is ketoconazole.

14. The composition of claim 7, wherein the surfactant is selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof.

15. A topical, foamable composition, consisting essentially of:
   (a) one or more antifungal agents in an amount of up to 5% by weight, the one or more antifungal agents being selected from the group consisting of an imidazole compound and a triazole compound, wherein the antifungal agent is capable of penetrating the upper layers of skin of a user;
   (b) a lower alcohol content of greater than 50% by weight and up to 90% by weight, wherein the lower alcohol is ethanol;
   (c) at least one surfactant in an amount of up to 5% by weight;
   (d) up to 5% by weight of a long chain alcohol or mixtures thereof;
   (e) up to 10% by weight propylene glycol; and
   (f) 5-95% by weight water;
   wherein the antifungal agent is retained in or on skin for a period of time sufficient to penetrate the epidermis of a user.

16. The topical, foamable composition of claim 15, wherein the imidazole compound is ketoconazole.

17. The topical, foamable composition of claim 15, wherein the surfactant is polyoxyethylene sorbitan monostearate.

18. The topical, foamable composition of claim 15, wherein the long chain alcohol is selected from the group consisting of cetyl alcohol, stearyl alcohol, and mixtures thereof.

19. A topical, foamable composition, consisting essentially of:
   (a) one or more antifungal agents in an amount of up to 5% by weight, the one or more antifungal agents being selected from the group consisting of an imidazole compound and a triazole compound;
   (b) ethanol at greater than 50% by weight and up to 90% by weight;
   (c) polyoxyethylene sorbitan monostearate in an amount of up to 5% by weight;
   (d) up to 5% by weight cetyl alcohol or stearyl alcohol or mixtures thereof;
   (e) up to 10% by weight propylene glycol; and
   (f) 5-95% by weight water;
   wherein the antifungal agent is retained in or on skin for a period of time sufficient to penetrate the epidermis of a user.

20. The topical, foamable composition of claim 19, wherein the imidazole compound is ketoconazole.

21. A method for treating fungal diseases, comprising:
   (a) providing a topical, foamable composition consisting essentially of
      one or more antifungal agents selected from the group consisting of an imidazole compound and a triazole compound, wherein the antifungal agent is capable of penetrating the upper layers of skin of a user,
      at least one surfactant,
      water, a lower alcohol content of greater than 10% by weight, a long chain alcohol, and hydrocarbon gas propellant in an amount of less than 60% by weight of the total composition, wherein the composition is a temperature sensitive quick breaking foam or mousse and has a residual non-volatile component content of less than 25% by weight; and
   (b) applying the topical, foamable composition to user's skin, whereupon the antifungal agent is retained in or on skin for a period of time sufficient to achieve skin penetration.

22. The method of claim 21, wherein the content of the residual non-volatile component is less than 10% by weight.

23. The method of claim 22, wherein the content of the residual non-volatile component is less than 6% by weight.

24. The method of claim 21, wherein the composition has a hydrocarbon gas propellant content of less than 10% by weight.

25. The method of claim 21, wherein the provided topical, foamable composition consists essentially of:
   up to 5% by weight of long chain alcohol;
   up to 10% by weight of propylene glycol;
   up to 5% by weight of the antifungal agent;
   up to 90% by weight of lower alcohol;
   up to 5% by weight of surfactant;
   5-95% by weight of water; and
   up to 20% by weight of a hydrocarbon gas propellant.

26. The method of claim 21, wherein the lower alcohol content is greater than 50% by weight.

27. The method of claim 21, wherein the lower alcohol is ethanol.

28. The method of claim 21, wherein the lower alcohol and water are present in a ratio of about 1.65 to about 1 by weight.

29. The method of claim 21, wherein the long chain alcohol is selected from the group consisting of cetyl alcohol, stearyl alcohol, and mixtures thereof.

30. The method of claim 21, wherein the antifungal agent is ketoconazole.

31. The method of claim 21, wherein the surfactant is selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof.

32. A topical, foamable composition consisting essentially of:
   (a) one or more antifungal agents selected from the group consisting of an imidazole compound and a triazole compound;
   (b) at least one surfactant;
   (c) a lower alcohol content of greater than 10% by weight;
   (d) water;
   (e) a long chain alcohol;
   (f) hydrocarbon gas propellant in an amount of less than 60% by weight; and
   wherein the composition is a temperature-sensitive, quick-breaking foam or mousse, and wherein the composition contains a residual non-volatile component content in an amount of less than 25% by weight.

33. The composition of claim 32, wherein the content of the residual non-volatile component is less than 10% by weight.

34. The composition of claim 33, wherein the content of the residual non-volatile component is less than 6% by weight.

35. The composition of claim 32, wherein the hydrocarbon gas propellant is present in an amount of less than 10% by weight.

36. The composition of claim 32, consisting essentially of:
    up to 5% by weight of long chain alcohol;
    up to 10% by weight of propylene glycol;
    up to 5% by weight of the antifungal agent;
    up to 90% by weight of lower alcohol;
    up to 5% by weight of surfactant;
    5-95% by weight of water; and
    up to 20% by weight of a hydrocarbon gas propellant.

37. The composition of claim 32, wherein the lower alcohol content is greater than 50% by weight.

38. The composition of claim 32, wherein the lower alcohol is ethanol.

39. The composition of claim 32, wherein the lower alcohol and water are present in a ratio of about 1.65 to about 1 by weight.

40. The composition of claim 32, wherein the long chain alcohol is selected from the group consisting of cetyl alcohol, stearyl alcohol, and mixtures thereof.

41. The composition of claim 32, wherein the antifungal agent is ketoconazole.

42. The composition of claim 32, wherein the surfactant is selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate and mixtures thereof.

43. A topical, foamable composition consisting essentially of:
    (a) one or more antifungal agents in an amount of up to 5% by weight, the one or more antifungal agents being selected from the group consisting of an imidazole compound and a triazole compound, wherein the antifungal agent is capable of penetrating the upper layers of skin of a user;
    (b) a lower alcohol content of greater than 50% by weight and up to 90% by weight, wherein the lower alcohol is ethanol;
    (c) at least one surfactant in an amount of up to 5% by weight;
    (d) up to 5% by weight of a long chain alcohol or mixtures thereof;
    (e) up to 10% by weight propylene glycol;
    (f) 5-34% by weight water; and
    (g) less than 10% by weight hydrocarbon gas propellant;
    wherein the antifungal agent is retained in or on skin for a period of time sufficient to penetrate the epidermis of a user.

44. The topical, foamable composition of claim 43, wherein the imidazole compound is ketoconazole.

45. The topical, foamable composition of claim 43, wherein the surfactant is polyoxyethylene sorbitan monostearate.

46. The topical, foamable composition of claim 43, wherein the long chain alcohol is selected from the group consisting of cetyl alcohol, stearyl alcohol, and mixtures thereof.

47. A topical, foamable composition consisting essentially of:
    (a) one or more antifungal agents in an amount of up to 5% by weight, the one or more antifungal agents being selected from the group consisting of an imidazole compound and a triazole compound;
    (b) ethanol at greater than 50% by weight and up to 90% by weight;
    (c) polyoxyethylene sorbitan monostearate in an amount of up to 5% by weight;
    (d) up to 5% by weight cetyl alcohol or stearyl alcohol or mixtures thereof;
    (e) up to 10% by weight propylene glycol;
    (f) 5 to about 34% by weight water; and
    (g) less than 10% by weight hydrocarbon gas propellant;
    wherein the antifungal agent is retained in or on skin for a period of time sufficient to penetrate the epidermis of a user.

48. The topical, foamable composition of claim 47, wherein the imidazole compound is ketoconazole.

49. A method for treating fungal diseases, comprising:
    (a) providing a topical, foamable composition which in use produces a temperature-sensitive, quick-breaking foam or mousse, the composition consisting essentially of:
       one or more antifungal agents selected from the group consisting of an imidazole compound and a triazole compound, wherein the antifungal agent is capable of penetrating the upper layers of skin of a user,
       at least one surfactant selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof,
       water, a lower alcohol, a long chain alcohol, and a residual non-volatile component content of less than 25% by weight; wherein the lower alcohol is ethanol with a content of greater than 50% by weight and the one or more antifungal agents is dissolved in the ethanol; and
    (b) applying the topical, foamable composition to user's skin, whereupon the antifungal agent is retained in or on skin for a period of time sufficient to achieve skin penetration.

50. A topical, foamable composition, consisting essentially of:
    (a) one or more antifungal agents selected from the group consisting of an imidazole compound and a triazole compound;
    (b) at least one surfactant selected from the group consisting of a quaternary compound, ethoxylated sorbitan stearate, ethoxylated sorbitan palm itate, ethoxylated sorbitan oleate, a nonyl phenol ethoxylate and a fatty alcohol ethoxylate, and mixtures thereof;
    (c) an ethanol content of greater than 50% by weight;
    (d) water;
    (e) a long chain alcohol;
    (f) a residual non-volatile component content of less than 25% by weight, wherein the one or more antifungal agents is dissolved in the ethanol; and
    wherein the composition produces a temperature-sensitive, quick-breaking foam or mousse when used.

51. A topical, foamable composition, consisting essentially of:
    (a) one or more antifungal agents in an amount of up to 5% by weight, the one or more antifungal agents being selected from the group consisting of an imidazole compound and a triazole compound, wherein the antifungal agent is capable of penetrating the upper layers of skin of a user;
    (b) a lower alcohol content of greater than 50% by weight and up to 90% by weight, wherein the lower alcohol is ethanol;
    (c) at least one surfactant in an amount of up to 5% by weight, the at least one surfactant being selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof;

(d) up to 5% by weight of a long chain alcohol or mixtures thereof;

(e) up to 10% by weight propylene glycol; and (f) 5-95% by weight water;

wherein the antifungal agent is retained in or on skin for a period of time sufficient to penetrate the epidermis of a user.

52. A method for treating fungal diseases, comprising:

(a) providing a topical, foamable composition consisting essentially of one or more antifungal agents selected from the group consisting of an imidazole compound and a triazole compound, wherein the antifungal agent is capable of penetrating the upper layers of skin of a user, at least one surfactant selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof, water, a lower alcohol content of greater than 10% by weight, a long chain alcohol, and hydrocarbon gas propellant in an amount of less than 60% by weight of the total composition, wherein the composition is a temperature sensitive quick breaking foam or mousse and has a residual non-volatile component content of less than 25% by weight; and (b) applying the topical, foamable composition to user's skin, whereupon the antifungal agent is retained in or on skin for a period of time sufficient to achieve skin penetration.

53. A topical, foamable composition consisting essentially of:

(a) one or more antifungal agents selected from the group consisting of an imidazole compound and a triazole compound;

(b) at least one surfactant selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof;

(c) a lower alcohol content of greater than 10% by weight;

(d) water;

(e) a long chain alcohol;

(f) hydrocarbon gas propellant in an amount of less than 60% by weight; and wherein the composition is a temperature-sensitive, quick-breaking foam or mousse, and has a residual non-volatile component content of less than 25% by weight.

54. A topical, foamable composition consisting essentially of:

(a) one or more antifungal agents in an amount of up to 5% by weight, the one or more antifungal agents being selected from the group consisting of an imidazole compound and a triazole compound, wherein the antifungal agent is capable of penetrating the upper layers of skin of a user;

(b) a lower alcohol content of greater than 50% by weight and up to 90% by weight, wherein the lower alcohol is ethanol;

(c) at least one surfactant in an amount of up to 5% by weight, the at least one surfactant being selected from the group consisting of a quaternary compound, ethoxylated sorbitan stearate, ethoxylated sorbitan palmitate, ethoxylated sorbitan oleate, a nonyl phenol ethoxylate and a fatty alcohol ethoxylate, and mixtures thereof;

(d) up to 5% by weight of a long chain alcohol or mixtures thereof;

(e) up to 10% by weight propylene glycol;

(f) 5-34% by weight water; and (g) less than 10% by weight hydrocarbon gas propellant;

wherein the antifungal agent is retained in or on skin for a period of time sufficient to penetrate the epidermis of a user.

\* \* \* \* \*